United States Patent [19]

Inoue et al.

[11] 4,266,055

[45] May 5, 1981

[54] TRIS(3-ACETYLTHIOPROPYL)ISOCYANU-RATE AND PREPARATION THEREOF

[75] Inventors: Yoshiharu Inoue, Osaka; Fumio Tanimoto, Kyoto; Hisao Kitano, Osaka, all of Japan

[73] Assignee: Nippon Kasei Chemical Co., Ltd., Tokyo, Japan

[21] Appl. No.: 147,522

[22] Filed: May 7, 1980

[51] Int. Cl.$^3$ .............................................. C07D 251/34
[52] U.S. Cl. ...................................................... 544/221
[58] Field of Search ............................................ 544/221

[56] References Cited

U.S. PATENT DOCUMENTS

| 3,676,440 | 7/1972 | Los | 260/248 NS |
| 3,821,098 | 6/1974 | Garratt et al. | 544/221 |
| 4,196,289 | 4/1980 | Saito et al. | 544/221 |

FOREIGN PATENT DOCUMENTS

| 1631 | | European Pat. Off. . |
| 54-47766 | 4/1979 | Japan . |

Primary Examiner—John M. Ford
Attorney, Agent, or Firm—Wegner & Bretschneider

[57] ABSTRACT

Disclosed in this invention are a novel compound tris(3-acetylthiopropyl)isocyanurate which can serve as an intermediate for the preparation of tris(3-mercaptopropyl)isocyanurate useful as a polymerization reaction regulator, crosslinking agent, curing agent, lubricant adjunct, etc., and a process for preparing the said compound, as well as a process for preparing tris(3-mercaptopropyl)isocyanurate using the said compound as an intermediate.

7 Claims, No Drawings

TRIS(3-ACETYLTHIOPROPYL)ISOCYANURATE AND PREPARATION THEREOF

BACKGROUND OF THE INVENTION

This invention relates to a novel compound tris (3-acetylthiopropyl) isocyanurate used as an intermediate for the preparation of tris(3-mercaptopropyl)isocyanurate and a process for preparing the said compound, as well as a process for preparing tris(3-mercaptopropyl)isocyanurate using the said compound as an intermediate.

Tris(3-mercaptopropyl)isocyanurate is not only useful as a regulator for various types of polymerization reactions but also usable as a synthetic resin material, crosslinking agent, vulcanizing agent, epoxy resin curing agent, lubricant adjunct, etc. However, there has been reported no industrially advantageous process for the preparation of tris(3-mercaptopropyl) isocyanurate.

Among the known arts for the preparation of the sulfur-containing tripropyl isocyanurate compounds by converting triallyl isocyanurate into a thiol, DT-OS 1,954,035 discloses a method in which alkylene thioglycol is added to triallyl isocyanurate, and U.S. Pat. No. 3,708,543 proposes a method in which 1-chloro-3-mercapto-2-propanol is added to triallyl isocyanurate.

However, the follow-up tests on these methods conducted by the inventors showed that it is difficult with these methods to obtain the reaction product with high purity, and hence it is not expedient to produce tris(3-mercaptopropyl)isocyanurate by utilizing these known methods.

As a result of further studies in search for an advantageous method for the preparation of tris(3-mercaptopropyl) isocyanurate, the inventors found that this substance can be produced in a most advantageous way by hydrolyzing tris(3-acetylthiopropyl)isocyanurate which is a novel compound derived from triallyl isocyanurate, and succeeded in attaining this invention on the basis of such finding.

An object of this invention, therefore, is to provide a novel compound which is used as an intermediate for the advantageous preparation of tris(3-mercaptopropyl)isocyanurate.

Another object of this invention is to provide a process for preparing the said novel compound which serves as an intermediate for the said purpose.

Still another object of this invention is to provide a process which is capable of producing tris(3-mercaptopropyl) isocyanurate advantageously by using the said novel intermediate compound.

DETAILED DESCRIPTION OF THE INVENTION

Tris(3-acetylthiopropyl)isocyanurate provided according to this invention is a novel compound having the following formula (I):

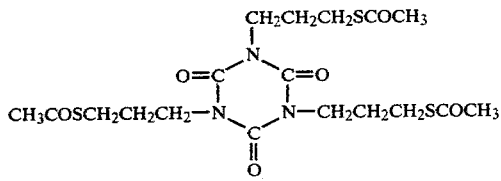

Tris(3-acetylthiopropyl)isocyanurate (hereinafter referred to as the compound of this invention) having the above-shown formula (I) is in the form of white crystals having a peculiar odor with a melting point of 64°–66° C. and is stable in the atmosphere. Also, this compound is easily soluble in acetone, benzene, chloroform, carbon tetrachloride and acetetic acid esters but scarcely soluble in petroleum type low-boiling solvents, ethanol and water.

This compound can be produced from a radical addition reaction of thiolacetic acid (thioacetic acid) to triallyl isocyanurate as depicted by the following reaction formula (II):

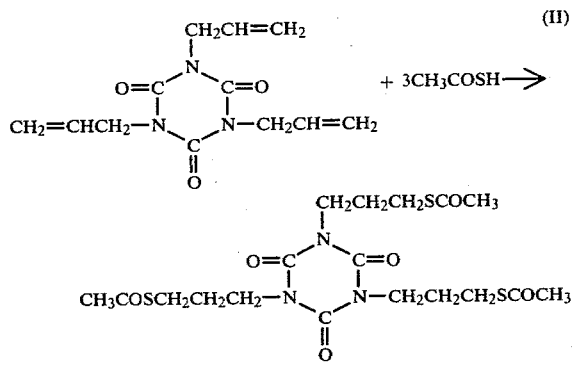

The said addition reaction for preparing the compound of this invention is carried out at a temperature of 0° to 150° C. in at least one solvent selected from hydrocarbons, ethers, ketones, lower fatty acids, esters, halogenated hydrocarbons, nitriles and acid amides. In order to promote said addition reaction to elevate the yield of the objective compound, the said reaction may be carried out (1) under application of the ultraviolet rays in the presence of a ketone compound as sensitizer, (2) at a temperature of 50°–150° C. in the presence of a non-oxidative organic radical reaction catalyst, or (3) under application of the ultraviolet rays in the co-presence of a ketone compound as sensitizer and a non-oxidative organic radical reaction catalyst.

The hydrocarbons usable as solvent in performing the said reaction according to this invention include: petroleum ethers, benzine, ligroin, gasoline, kerosine, light oil, pentane, hexane, heptane, octane, cyclohexane, methylcyclohexane, benzene, toluene, xylene, trimethylbenzene, ethylbenzene and cumene, and the ethers also usable for the said purpose include dimethyl ether, diethyl ether, dipropyl ether, dibutyl ether, methyl ethyl ether, methyl propyl ether, methyl butyl ether, anisole, phenetole, methylal, ethylal, tetrahydrofuran, dioxane, dimethoxyethane, diethoxyethane, methoxyethyl acetate and ethoxymethyl acetate. Examples of the ketone compounds usable as solvent in the said reaction include acetone, methyl ethyl ketone, diethyl ketone, dipropyl ketone, methyl propyl ketone, methyl butyl ketone, cyclopentanone, cyclohexanone, acetophenone and methylacetophenone, and examples of the lower fatty acids include formic acid, acetic acid, propionic acid and butyric acid. The esters usable in this invention include methyl formate, ethyl formate, propyl formate, butyl formate, amyl formate, methyl acetate, ethyl acetate, propyl acetate, butyl acetate, methyl propionate, ethyl propionate, propyl propionate, methyl butyrate, propyl butyrate, butyl butyrate, ethylene glycol diacetate, propylene glycol diacetate, butylene glycol diacetate, glycerin triacetate and methylene diacetate, and the halogenated hydrocarbons include methylene chloride, chloroform, carbon tetrachloride, methane fluoride chloride (freon), ethane fluoride chloride (freon), ethylene chloride, trichlene, perchlene, methylchloroform, dichloropropane, chloroalkane, chlorobenzene, dichlorobenzene and chlorotoluene, and the examples of acid amides are acetonitrile, benzonitrile, formamide, dimethylformamide and dimethylacetamide.

These solvents may be used either singly or in combination of two or more. Also, they may be used in all compound forms such as n-, iso-, secondary, tertiary, ortho-, meta- and para-. Among these solvents, the following are preferred in industrially practicing the said addition reaction according to this invention: petroleum ether, benzine, ligroin, gasoline, hexane, heptane, cyclohexane, benzene, toluene, xylene, ethyl ether, dipropyl ether, dimethoxyethane, tetrahydrofuran, dioxane, acetone, methyl ethyl ketone, methyl butyl ketone, formic acid, acetic acid, methyl formate, methyl acetate, methylene chloride, chloroform, carbon tetrachloride, methylchloroform, chlorobenzene, acetonitrile and dimethylformamide. Particularly, the ketone compounds can further promote the reaction since they act as a sensitizer as said before. In case of using the above-cited substances other than the ketone compounds as solvent, the following ketone compounds may be incorporated as sensitizer: acetone, methyl ethyl ketone, diethyl ketone, dipropyl ketone, dibutyl ketone, methyl propyl ketone, methyl butyl ketone, mesityl oxide, cyclopentanone, cyclohexanone, acetophenone, propiophenone, butyrophenone, benzophenone, dibenzyl ketone, halogen-oacetophenone, methylacetophenone, methoxyacetophenone, dimethylaminoacetophenone, nitroacetophenone, hydroxyacetophenone, anthraquinone, naphthoquinone, benzoquinone, cumoquinone, benzanthraquinone, fluorenone, benzyl, benzoin, nitrofluorein, dinitrofluorein, nitroacenaphthene, benzoylacenaphthene, acethylacetone, diacetyl, benzoylacetone, dibenzoyl, acetoacetic acid ester, methylbenzophenone, halogenobenzophenone, methoxybenzophenone, dimethylaminobenzophenone, aminobenzophenone, nitrobenzophenone, hydroxybenzophenone, and one or a mixture of the compounds selected from the group consisting of acyl halides, anhydrous organic acids and polyacylated compounds derived from ketene by a Friedel-Crafts reaction. Among these ketone compounds, acetone, methyl ethyl ketone, acetophenone, benzophenone or their nuclear substituents are particularly preferred for use as sensitizer because of availability at low cost.

The term "non-oxidative organic radical reaction catalyst" used for promoting the said addition reaction according to this invention referes to the radical reaction catalysts excluding those which can act as oxidizer such as oxygen, ozone, persulfates, percarbonates, perchlorates, perborates, permanganates, organic peracids, hydrogen peroxide and peroxides exclusive of ozonides, and the examples of such organic radical reaction catalysts are: benzoyl peroxide, para- (or ortho- or meta-)chlorobenzoyl peroxide, para- (or ortho- or meta-)methylbenzoyl peroxide, para-methoxy-benzoyl peroxide, para-nitrobenzoyl peroxide, methyl ethyl ketone peroxide, cumene hydroperoxide, tert-butyl hydroperoxide, di-tert-butyl peroxide, caproyl peroxide, isooctanoyl peroxide, lauroyl peroxide, methyl isobutyl ketone peroxide, cyclohexanone peroxide, acetyl peroxide, propionyl peroxide, 2,4-dichlorobenzoyl peroxide, tert-butylcumyl peroxide, dicumyl peroxide, tert-butyl peracetate, diisopropyl peroxydicarbonate, di-sec-butyl peroxydicarbonate, azobis-2,4-dimethylvaleronitrile, azobis-2-methylbutyronitrile, azobis-isobutyronitrile, 2,2'-azobis-(2-amidinopropane) dihydrochloride, azobis-2-cycloalkylidene cyanide and the compounds of the type in which the said cyano groups have been converted into carbomethoxyl or carboethoxyl groups. These compounds may be used either singly or in combination as the said organic radical reaction catalyst.

The ultraviolet rays used for promoting the reaction in this invention are those having a wavelength ($\lambda$) of 200–500 nm, preferably 250–400 nm, and the ordinary ultraviolet lamp, mercury lamp, fluorescent lamp, xenon lamp, tungsten lamp, sun rays or arc lamp may be used for the said purpose.

In preparation of tris(3-acetylthiopropyl)isocyanurate according to the above-shown reaction formula (II), triallyl isocyanurate used as a starting material is preferably one having a purity of at least 95%. Particularly, it is advised to select a material whose contents of primary amine, secondary amine and triallyl cyanurate are minimized.

The thiolacetic acid used for the addition reaction with the said triallyl isocyanurate is one synthesized by a reaction of hydrogen sulfide with acetic anhydride, and it is possible to use commercially available thiolacetic acid as well as an acetic acid solution of thiolacetic acid obtained by reacting acetic anhydride and hydrogen sulfide. It is desirable that the thiolacetic acid used here should contain no such impurities as sulfur oxides, sulfuric acid and alkali sulfides.

In the said addition reaction for synthesizing tris(3-acetylthiopropyl)isocyanurate according to this invention, since the starting material triallyl isocyanurate is having unsaturated functional groups, is per se highly polymeric, there is a risk of causing by-production of 2-acetylthiopropyl compounds and/or side reactions such as allyl rearrangement reaction or dimerization reaction due to formation of thioether. In this invention, therefore, in order to prevent such side reactions, there are used triallyl isocyanurate (starting material) and thiolacetic acid of high purity as said above, and also the reaction is carried out in the presence of a solvent such as cited above and under a specified temperature condition. It is also attempted to add a sensitizer and a non-oxidative organic radical reaction catalyst such as mentioned above and to apply the ultraviolet rays.

The addition reaction in this invention is carried out under a temperature condition of 0°–150° C., preferably 5°–100° C. If the reaction temperature is below 0° C., the reaction is sluggish and a long time is required till it is completed, so that air might be absorbed into the reaction system during such a long time reaction to give rise to excessive side reaction products such as said above. On the other hand, if the reaction temperature exceeds 150° C., it becomes necessary to elevate the pressure applied to the reaction system because the boiling point of thiolacetic acid, which is one of the reaction material, is 93° C., and this promotes polymerization of triallyl isocyanurate which is the other reaction material. As the solvents used in this invention, such as mentioned above, are inert to the reaction materials, there is no fear of inducing any unexpected side-reaction, and also there is little chance of air absorption into the reaction system because of low air solubility. It is to be noted in this connection that such substances as water, alcohol, nitrohydrocarbons, aldehydes, dimethyl sulfoxide, dimethyl sulfone, tetramethyl sulfone and tertiary amines, which are often used as solvent for the synthesis of organic compounds, can cause unexpected reactions with thiolacetic acid or may partially oxidize thiolacetic acid, and moreover, they have high air solubility, so that these solvents can not be used singly in this invention. It is, however, possible to use these substances in admixture with the solvents employed in this invention provided that the said substances are mixed in an amount not exceeding 30%.

The sensitizers used in this invention, such as above-mentioned, are excited by absorbing light in the reaction system and the energy thus absorbed is transferred into the reaction materials to expedite the addition reaction of this invention. It should be understood, therefore, that the said sensitizers are essentially different from the optical catalysts which do not absorb effective light but merely act to promote the reaction. The ketone compounds employed as a sensitizer for this purpose are preferably used in an amount of 0.1 to 10% by weight based on the reaction mixture, and in case of using a protonic solvent such as acetic acid as solvent in the reaction system of this invention, it is desirable to increase the loading of such solvent.

The non-oxidative organic radical reaction catalyst used in this invention serves as a radical initiator of the addition reaction of this invention. In case of using such catalyst, the reaction temperature is preferably adjusted to 50°–150° C., more preferably 50°–120° C., at which the said catalyst is decomposed in the reaction mixture. The amount of the said radical reaction catalyst added is preferably within the range of 0.05–5.0% by weight based on the reaction mixture. It should be noted that too much loading of the catalyst or too high reaction temperature induces polymerization of triallyl isocyanurate itself to cause resinification.

Application of ultraviolet rays in this invention has a role of supplying the electronic energies required to elevate the ground state of the reaction material thiolacetic acid or trially isocyanurate to their excited state, and consequently, the said reaction materials are thus activated to undergo the desired reaction.

According to this invention, tris(3-acetylthiopropyl) isocyanurate can be produced in a high yield, without inducing substantially any side-reaction, by reacting triallyl isocyanurate and thiolacetic acid under the said reaction conditions for a period of about 10 to 1,000 minutes under the normal pressure or by applying only a slight pressure of less than 10 atm. by using an ordinary reaction apparatus.

The tris(3-acetylthiopropyl)isocyanurate preparation process according to this invention may be either batch type or continuous type. In the case of the batch type process, in view of the structural formula of tris(3-acetylthiopropyl)isocyanurate, it is essential for improving the yield of the objective product to feed thiolacetic acid in an amount of 3 mols or more to 1 mol of triallyl isocyanurate into the reactor, but in certain types of reaction operation (for example, in the case of a continuous system), thiolacetic acid may be initially fed into the first stage reactor in an amount of 30 to 60% by weight of the total amount of thiolacetic acid to be reacted, and the remaining amount of thiolacetic acid may be reacted in the second and/or third stage reactor.

The reaction product is further subjected to a necessary chemical treatment such as distillation, extraction or recrystallization to separate tris(3-acetylthiopropyl)isocyanurate from the said reaction products.

The tris(3-acetylthiopropyl)isocyanurate thus obtained can be hydrolyzed to form tris(3-mercaptopropyl)isocyanurate.

The reaction of the said hydrolysis may be accomplished by acidic hydrolysis, neutral hydrolysis or alkaline hydrolysis. The acidic hydrolysis can be performed by using a non-oxidative mineral acid such as hydrochloric acid, sulfuric acid, phosphoric acid, etc., as catalyst at a reaction temperature of 20°–110° C. and with an acid concentration of about 0.2–150%. The neutral hydrolysis is performed under pressure in hot water of higher than 100° C., but the solution becomes acidic as acetic acid is librated. The alkaline hydrolysis is carried out at 40°–120° C. in the presence of ammonia water, sodium hydroxide, potassium hydroxide, sodium carbonate, potassium carbonate, calcium hydroxide, calcium carbonate or the like. When a calculated amount of an alkali exists, an alkali acetate is produced, but in case an excess amount of an alkali exists, there is produced the corresponding mercaptide, so that, in this case, it needs to acidify the reaction product after completion of the reaction to liberate mercaptan. Any of the said reactions can be accomplished relatively easily, but it is free to add a small amount of a surfactant for the purpose of expediting dispersion of the reaction material in water for further accelerating the hydrolysis. The reaction product is subjected to a suitable chemical treatment such as solvent extraction, vapour distillation, oil phase separation, salting-out or centrifugation to separate tris(3-mercaptopropyl) isocyanurate ester from the said reaction products, and this ester is refined by suitable means such as water washing, drying, decoloring, distillation or recrystallization. What is to be noted here is that the whole operations between hydrolysis and the final refining should preferably be performed under a non-oxidative atmosphere to a maximum possible degree so as to prevent the contamination of the objective product due to mixing of disulfide which may be caused by the presence of the oxidizer.

The term "non-oxidative atmosphere" as used herein means a reaction atmosphere excluding oxidizers, such as organic active halogen compounds, hydrogen peroxide, permanganates chromic acid, nitric acid, halogens, organic peracids, persulfuric acid, selenium dioxide, iron chloride, potassium ferricyanide, oxygen (air) and ozone, which may oxidize mercaptan when hydrolyzing the reaction product obtained from the reaction of triallyl isocyanurate with thiolacetic acid, that is, tris(3-mercaptopropyl) isocyanurate, or when refining tris(3-mercaptopropyl)isocyanurate obtained by the hydrolysis. It is advisable to actually use an inert gas such as nitrogen or argon for the said non-oxidative atmosphere.

The hydrolysis is preferably performed on the solvent-removed reaction product containing tris(3-acetylthiopropyl) isocyanurate obtained as said above according to this invention. In the case of acidic hydrolysis for example, the said solvent-removed reaction product is dissolved in methanol, and the solution is mixed with concentrated hydrochloric acid and heated, and then after neutralizing the obtained product, methanol is distilled off in a nitrogen atmosphere to obtain tris(3-mercaptopropyl) isocyanurate. In the case of alkaline hydrolysis, the solvent-removed reaction product is mixed with an aqueous solution of sodium hydroxide and heated, and after cooling, the resultant product is made acidic with concentrated hydrochloric acid and then subjected to solvent extraction (by using benzene for example), and the extract solution thus obtained is distilled under an argon stream to obtain tris(3-mercaptopropyl)isocyanurate.

Tris(3-mercaptopropyl)isocyanurate obtained by hydrolyzing tris(3-acetylthiopropyl)isocyanurate and then refining the hydrolyzed product as said above is a viscous heavy liquid having a slight odor, and this liquid is turned into a glassy liquid upon cooling. This compound is soluble in organic solvents and aqueous alkaline solutions, and when reacted with 2,4-dinitrofluorobenzene, it gives the corresponding trithioether (melting point: 104° C.).

Tris(3-mercaptopropyl)isocyanurate has the following structural formula (III):

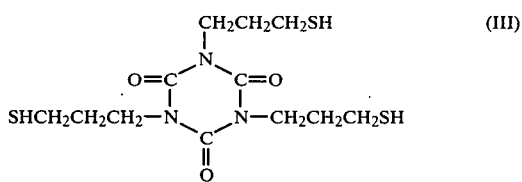

As described above, it is possible according to this invention to advantageously produce tris(3-mercaptopropyl)isocyanurate by first producing as an intermediate tris(3-acetylthiopropyl)isocyanurate by reacting triallyl isocyanurate and thiolacetic acid, and then hydrolyzing this intermediate.

The invention is described in further detail hereinbelow by way of the examples thereof.

PREPARATION OF TRIS(3-ACETYLTHIOPROPYL)ISOCYANURATE

Example 1

A mixture of 5.3 g (0.021 mol) of triallyl isocyanurate, 5.8 g (0.076 mol) of thiolacetic acid and 150 ml of benzene was placed in a reactor provided with a high-pressure mercury lamp, and irradiated with stirring under a nitrogen stream at 25° C. for 5 hours. Benzene was distilled off from the reaction mixture and the residue was dissolved in methanol and recrystallized therefrom to obtain 0.6 g (6.0% yield) of tris(3-acetylthiopropyl)isocyanurate (I). This compound was in the form of white needle-like crystals with a melting point of 64.0°-66.0° C. and its structure was identified as follows:

(1) Elemental analysis :
Calcd. for $C_{18}H_{27}N_3O_6S_3$: C, 45.28%; H, 5.66%; N, 8.81%; O, 20.13%; S, 20.13%. Found: C, 45.46%; H, 5.86%; N, 8.80%; O, 19.99%; S, 19.98%.

The calculated and found values agree with each other within the range of errors in the analytical experiment.

(2) Measurement of nuclear magnetic resonance absorption band
(n.m.r.)
(Using $CDCl_3$), 6.1 $\tau$ (triplet, 2H), 7.2$\tau$ (triplet, 2H), 7.7$\tau$ (singlet, 3H), 7.8-8.3$\tau$ (quintet, 2H).

(3) Measurement of infrared absorption band (I.R.):
(Nujol method), 1680 cm$^{-1}$ (stretching vibration of two
C=O bonds of =N—CO—N= and —S—CO—CH$_3$), 1130 cm$^{-1}$ and
1100 cm$^{-1}$ (antisymmetric and symmetric stretching vibrations of C—S—C bond of C—S—CO—CH$_3$), 760 cm$^{-1}$
(stretching vibration of C—N bond of =N—CO—N=).

The structure and bonding positions of tris(3-acetylthiopropyl)isocyanurate were determined from the foregoing measurements.

(4) Synthesis of confirmed compound: Tris(3-acetylthiopropyl)isocyanurate (I) was put into an alcoholic aqueous solution of potassium hydroxide and boiled, and after adding 2,4-dinitrochlorobenzene, the mixture was again boiled. The reaction mixture was charged into water and the precipitated crystals were collected and recrystallized from alcohol to obtain tris[3-(2,4-dinitrophenyl)-thiopropyl]isocyanurate having a melting point of 103°-104° C. The elemental analysis and the n.m.r. and i.r. tests on this product confirmed that the starting material was obviously tris(3-acetylthiopropyl)isocyanurate (I).

Example 2

Triallyl isocyanurate (124 g., 0.5 mol), 126 g (1.7 mols) mols) of thiolacetic acid and 1.5 litres of acetone serving as solvent/sensitizer were put into a reactor provided with a high-pressure mercury lamp, and the mixture was irradiated with stirring under a nitrogen stream to effect a a reaction at 20° C. for 2 hours. Then acetone was distilled off from the reaction mixture and the residue was dissolved in methanol and recrystallized therefrom to obtain 230 g (96% yield) of tris(3-acetylthiopropyl) isocyanurate (I).

Example 3

The process of Example 2 was repeated but by using 1.5 litres of the solvents and the sensitizers shown in Table 1 below instead of acetone, consequently obtaining tris(3-acetylthiopropyl) isocyanurate (I) in the yields shown in the same table.

TABLE 1

| Solvent | Sensitizer (amount used, g) | Yield of (I) (%) |
| --- | --- | --- |
| Toluene | Benzophenone (5) | 94 |
| Cyclohexane | Benzophenone (5) | 96 |
| Methyl ethyl ketone | —* | 98 |
| Acetophenone | —* | 99 |
| Acetic acid | p-chlorobenzophenone (10) | 90 |
| Chloroform | p-methylbenzophenone (10) | 88 |

(Note)
*:The solvent doubled as sensitizer.

Example 4

Triallyl isocyanurate (5.3 g., 0.021 mol) and an acetic acid solution containing 5.8 g (0.076 mol) of thiolacetic acid (a reaction solution obtained according to the method described in Organic Sythesis, Vol. 31, p. 105 (1951), by blowing hydrogen sulfide into acetic anhydride) were put into a sealed pressure-resistant glass tube, and the mixture was reacted at 90° C. for 10 hours in the presence of the radical reaction catalysts shown in Table 2 below. The reaction mixture was charged into water and subjected to either extraction, and tris(3-acetylthiopropyl) isocyanurate (I) was collected by means of distillation of ether and subsequently recrystallization, and the yield was measured.

TABLE 2

| Radical reaction catalyst (amount used, g) | Yield of (I) (%) |
|---|---|
| Benzoyl peroxide (0.01) | 68 |
| 2,4-dichlorobenzoyl peroxide (0.01) | 75 |
| Azobisisobutyronitrile (0.02) | 81 |
| Azobis-2,4-dimethylvaleronitrile (0.02) | 80 |
| Cyclohexanone perxoide (0.01) | 71 |
| Dicumyl peroxide (0.01) | 65 |

Example 5

Triallyl isocyanurate (5.3 g., 0.021 mol), 5.8 g (0.076 mol) of thiolacetic acid and 10 ml of the solvents as well as the sensitizers or radical reaction catalysts shown in Table 3 below were put into a sealed pressure-resistant glass tube and the mixture was reacted at 60° C. for 4 hours under the direct sun-beam and then treated in a similar manner to Example 4, whereby tris(3-acetylthiopropyl)isocyanurate (I) was obtained in the yields shown in Table 3.

TABLE 3

| Solvent | Sensitizer or radical catalyst (amount used, g) | Yield of (I) (%) |
|---|---|---|
| Benzene | Acetone (0.5) | 75 |
| Xylene | Methyl isobutyl ketone (0.7) | 62 |
| Dimethoxyethane | Acetophenone (0.8) | 78 |
| Tetrahydrofuran | Benzophenone (0.8) | 80 |
| Carbon tetrachloride | Benzoyl peroxide (0.01) | 52 |
| Chlorobenzene | Azobisisobutyronitrile (0.01) | 66 |
| Ethyl acetate | p-methoxyacetophenone (0.4) | 69 |
| n-heptane | o-methylacetophenone (0.5) | 68 |
| Acetonitrile | Dibenzyl ketone (1.0) | 84 |
| Dimethylformamide | p,p-dimethoxybenzophenone (0.4) | 73 |
| Acetone | Nitrofluorenone (0.5) | 92 |
| Ether/acetone (1:1) | Anthraquinone (0.5) | 85 |

Example 6

Triallyl isocyanurate (10.5 g., 0.042 mol),10.5 g (0.138 mol) of thiolacetic acid, 0.5 g (0.002 mol) of benzoyl peroxide, 0.04 g (0.0002 mol) of benzophenone and 300 ml of benzene were put into a reactor provided with a high-pressure mercury lamp and a Pyrex Clear chemical glass filter, and the mixture was irradiated with stirring under a nitrogen stream at 25° C. for one hour. Benzene was distilled off and recovered from the reaction mixture and the residue was dissolved in methanol and recrystallized therefrom to obtain 18.6 g (97.5% yield) of tris(3-acetylthiopropyl)isocyanurate (I).

PREPARATION OF TRIS(3-MERCAPTOPROPYL)ISOCYANURATE

Example 7

Triallyl isocyanurate (124 g), 126 g of thiolacetic acid, 1,000 g of acetone and 500 g of acetic acid were put into a flask so designed as to allow application of ultraviolet rays, and the mixture was reacted at 30° C. for 100 minutes under irradiation of ultraviolet rays. The reaction mixture was distilled under reduced pressure to recover 950 g of acetone and 470 g of acetic acid, and the residue was dissolved in about 10 times as much amount of methanol, then treated with 50 g of centrated hydrochloric acid and refluxed under boiling for 6 hours. Then the reaction mixture was neutralized by adding anhydrous sodium carbonate and passed through a column packed with neutral active alumina. Methanol was distilled off under a nitrogen stream from the obtained methanol solution and the residue was dried under reduced pressure to obtain tris(3-mercaptopropyl)isocyanurate with m.p. of -27 to -26° C. and $n_D^{29} 1.5561$ in a yield of approximately 98%. Anal. Calcd. for $C_{12}H_{21}N_5O_3S_3$: C, 41.03%; H, 5.98%; N, 11.97%; S, 27.35%. Found: C, 41.28%; H, 6.08%; N, 11.63%; S, 27.10%. This compound was identified as tris(2,4-dinitrophenyl)thioether (m.p.=104° C.) from the reaction with 2,4-dinitrochlorobenzene or 2,4-dinitrofluorobenzene.

The n.m.r. and i.r. spectra of tris(3-mercaptopropyl) isocyanurate were as follows:

n.m.r. (CDCl₃); τ:
6.0 (triplet, 2H), 7.0–7.6 (multiplet, 2H),
7.8–8.3 (quintet, 2H), 8.4–8.7 (triplet, 1H).
i.r. (cm⁻¹):
2980, 2560, 1680, 1440, 760.

Example 8

Triallyl isocyanurate (124 g), an acetic acid solution containing 120 g of thiolacetic acid (a solution obtained by dissolving hydrogen sulfide in acetic anhydride according to the method shown in Organic Synthesis, Vol. 4, p. 928 (1967), John Wiley and Sons, Inc.) and 200 g of methyl ethyl ketone were put into a flask so designed as to allow irradiation of ultraviolet rays, and the mixture was stirred at 25°–35° C. for 28 hours under irradiation of ultraviolet rays and then distilled under reduced pressure to recover the substantial portions of acetic acid and methyl ethyl ketone, and the residue was mixed with 400 ml of a 5% aqueous solution of sodium hydroxide and boiled for one hour. After cooling, the reaction mixture was made acidic with concentrated hydrochloric acid and extracted with benzene and the extract solution was dried with anhydrous magnesium sulfate and distilled under an argon stream, whereby tris(3-mercaptopropyl) isocyanurate was obtained as a viscous distillation residue. This residue was decolored and refined by using active carbon and activated clay to obtain an oily substance with m.p. of −27° to −26° C. and $n_D^{29} 1.5559$ in a yield of about 92%. This substance was identified as 2,4-dinitrophenyl ether.

What is claimed is:

1. Tris(3-acetylthiopropyl) isocyanurate represented by the following formula:

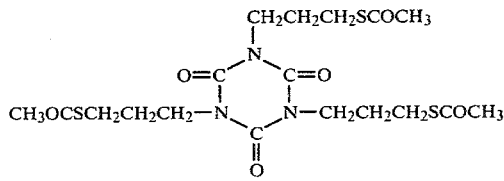

2. A process for producing tris(3-acetylthiopropyl) isocyanurate comprising bringing triallyl isocyanurate and thioacetic acid into reaction at a temperature of 0° to 150° C. in at least one polar solvent selected from the group consisting of hydrocarbons, ethers, ketones, lower fatty acids, esters, halogenohydrocarbons, nitriles and acid amides.

3. A process for producing tris(3-acetylthiopropyl)isocyanurate comprising bringing triallyl isocyanurate and thioacetic acid into reaction in the presence of a non-oxidative organic radical reaction catalyst at a temperature of 50° to 150° C. in at least one polar solvent selected from the group consisting of hydrocarbons, ethers, ketones, lower fatty acids, esters, halogenohydrocarbons, nitriles and acid amides.

4. A process for producing tris(3-acetylthiopropyl) isocyanurate comprising bringing triallyl isocyanurate and thioacetic acid into reaction at a temperature of 0° to 150° C. in at least one polar solvent selected from the group consisting of hydrocarbons, ethers, lower fatty acids, esters, halogenohydrocarbons, nitriles and acid amides in the presence of a ketone as a sensitizer under the irradiation of ultraviolet rays.

5. A process for producing tris(3-acetylthiopropyl) isocyanurate comprising bringing triallyl isocyanurate and thioacetic acid into reaction at a temperature of 0° to 150° C. in at least one polar solvent selected from the group consisting of hydrocarbons, ethers, lower fatty acids, esters, halogenohydrocarbons, nitriles and acid amides in the presence of a non-oxidative organic radical reaction catalyst and a ketone as a sensitizer under the irradiation of ultraviolet rays.

6. The process according to any one of claims 2 to 5, wherein said ketone is selected from the group of consisting of acetone, methyl ethyl ketone, acetophenone, benzophenone, p-chlorobenzophenone, p-methylbenzophenone, methyl isobutyl ketone, p-methoxyacetophenone, o-methylacetophenone, dibenzyl ketone, p,p-dimethoxybenzophenone, nitrofluorenone and anthraquinone.

7. The process according to claim 3 or 5, wherein the said non-oxidative organic radical reaction catalyst is selected from the group consisting of benzoyl peroxide, p-chlorobenzoyl peroxide, o-chlorobenzoyl peroxide, m-chlorobenzoyl peroxide, p-methylbenzoyl peroxide, o-methylbenzoyl peroxide, m-methylbenzoyl peroxide, p-methoxybenzoyl peroxide, p-nitrobenzoyl peroxide, methyl ethyl ketone peroxide, cumene hydroperoxide, tert-butyl hydoperoxide, di-tert-butyl peroxide, caproyl peroxide, isooctanoyl peroxide, lauroyl peroxide, methyl isobutyl ketone peroxide, cyclohexanone peroxide, acetyl peroxide, propionyl peroxide, 2,4-dichlorobenzoyl peroxide, tert-butylcumyl peroxide, dicumyl peroxide, tert-butyl peracetate, diisopropyl peroxydicarbonate, di-sec-butyl peroxydicarbonate, azobis-2,4-dimethylvaleronitrile, azobis-2-methylbutyronitrile, azobisisobutyronitrile, 2,2'-azobis(2-amidinopropane) dihydrochloride and azobis-2-cycloalkylidene cyanide.

* * * * *